(12) United States Patent
Bertz et al.

(10) Patent No.: US 6,225,485 B1
(45) Date of Patent: May 1, 2001

(54) HIGH PURITY ADDUCT OF CASTOR OIL AND MALEIC ANHYDRIDE

(75) Inventors: Steven H. Bertz, Mendham; Frank M. Miksza, Colonia, both of NJ (US); Elliott Zucker, Shohola, PA (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/343,663

(22) Filed: Jun. 29, 1999

(51) Int. Cl.$^7$ .......................... C07C 67/08; C07C 69/60; A61K 7/48; A61K 7/075

(52) U.S. Cl. ...................... 554/148; 424/70.31; 514/547; 514/847; 554/219; 554/164

(58) Field of Search .................... 424/401, 70.31; 514/547, 847; 549/233, 262, 253; 554/219, 148

(56) References Cited

U.S. PATENT DOCUMENTS 2,551,352 * 5/1951 Tawney .................................. 260/23

FOREIGN PATENT DOCUMENTS

445688 * 2/1975 (SU) .

* cited by examiner

*Primary Examiner*—Bernard Dentz
(74) *Attorney, Agent, or Firm*—Walter Katz; William J. Davis; Marilyn J. Maue

(57) ABSTRACT

What is shown is a high purity adduct of castor oil and a cyclic carboxylic acid anhydride, characterized by the absence of free acid anhydride, which is used in personal care products. The adduct is made by a process, without side reactions, which includes (a) reacting castor oil and cyclic carboxylic acid anhydride at a temperature of 75–120° C. for 4 to 24 hours, and then (b) continuing the reaction at room temperature for at least 1 week to react any remaining maleic anhydride. Skin and hair care formulations of such adducts are also described.

10 Claims, No Drawings

HIGH PURITY ADDUCT OF CASTOR OIL AND MALEIC ANHYDRIDE

BACKGROUND OF THE INVENTION

1. Field of the Invention

This invention relates to personal care products, and, more particularly, to skin and hair care compositions containing a high purity adduct of castor oil and a cyclic carboxylic acid anhydride, which provides a substantive skin feel for the user, and to a method for making such useful adducts with no free acid anhydride therein.

2. Description of the Prior Art

Reaction products of castor oil and dehydrated castor oil with maleic anhydride have been disclosed in the literature. However, they usually involve other components in the reaction mixture which are present to provide the product with suitable properties for use, for example, as hardening agents for epoxy resins, or for leather fat liquoring, or as emulsifiers for the polymerization of vinyl chloride and other aqueous polymer compositions, and as lubricants for rolling mills. For example, SU 445688, published Feb. 26, 1975, described paint compositions containing the reaction product of castor oil and maleic anhydride having a substantial amount of free maleic anhydride, particularly, about 1–4%; and DE 3202408, published Aug. 4, 1983, disclosed the use of castor oil and cyclic anhydride adducts as flexibilizing agents for epoxy resins.

Accordingly, it is an object of the invention to provide a high purity adduct of castor oil and a cyclic carboxylic acid anhydride characterized by the absence of free acid anhydride, and a process for making such advantageous adduct, which is carried out with no significant side reactions.

Another object of the invention is to afford personal care products, particularly for skin care, which provide a highly substantive skin feel, as well as moisturization benefits, and hair care, particularly hair conditioning, in both leave-on and rinse-off applications, which products include a high purity adduct of castor oil and carboxylic acid anhydride having no free acid anhydride.

These and other objects and features of the invention will be made apparent from the following description thereof.

SUMMARY OF THE INVENTION

The invention herein provides a high purity adduct of castor oil and a cyclic carboxylic acid anhydride characterized by the absence of free acid anhydride therein. The mole ratio of anhydride to castor oil in the high purity adduct is in the range of 0.5:1 to 2.5:1, with 1:1 being the preferred ratio.

The adduct is made by a process which is carried out with no significant side reactions, including (a) reacting castor oil and cyclic carboxylic acid anhydride at a temperature of 75–120° C. for 4 to 24 hours, and then (b) continuing the reaction at room temperature for at least 1 week to react any remaining acid anhydride. Preferably step (a) is carried out at about 100° C. for about 6–8 hours, and (b) is carried out at room temperature for about 1–2 weeks. Preferably, the product of (a) is held at 50–80° C. for 24 hours while drumming the batch, as it decreases the time required for step (b).

The product of such a process is the desired high purity, 1:1 adduct with no free acid anhydride detectable by ordinary gas chromatography (GC).

The adduct of the invention finds commercial application in personal care products, which are suitable for both leave-on and rinse-off modes of application. These include skin care cleansing and treatment products, which provide the user with a substantive skin feel and moisturization benefits; and in hair conditioning compositions.

DETAILED DESCRIPTION OF THE INVENTION

Castor oil is one of three triglycerides that contain principally one fatty acid; it is about 90% ricinoleic acid, or 12-hydroxyoleic acid. The other two are tung oil, which is about 80% eleostearic acid, and oiticica oil, which is about 80% licanic acid. The hydroxyl group of the ricinoleic acid reacts like a typical secondary alcohol, i.e. it can be eliminated or esterified.

Elimination is a dehydration reaction which gives rise to about a 60:40 mixture of non-conjugated-to-conjugated linoleic acid isomers in the product, which is called dehydrated castor oil and sold as a drying oil. The conjugated linoleic acid residues are suitable for a Diels-Alder reaction with dienophiles such as maleic anhydride, maleic acid or fumaric acid. Both dehydration and Diels-Alder reactions are considered undesirable side reactions in this invention. Crosslinking is another undesirable side reaction, which becomes significant in the temperature range of 125–150° C.

Esterification of castor oil can occur by reaction with an anhydride. When the anhydride is cyclic, e.g. maleic or succinic anhydride, the carboxylic acid group formed during the reaction remains attached in the product. At any given temperature, an equilibrium is established between starting materials and product where the higher the temperature, the more starting materials are observed. For example, at 100° C., the equilibrium concentration of maleic anhydride in such a reaction is 1% of the starting amount. At room temperature, the equilibrium is far on the side of the desired product; however the reaction time is inordinately long.

In this invention, reaction between castor oil and cyclic carboxylic acid anhydride is suitably run at about 75–120° C., preferably at about 100° C. for maleic anhydride and 120° C. for succinic anhydride. The reactions reach 98–99% conversion in 6–8 hours. Upon cooling slowly and standing for a day or two at room temperature, the conversion is >99%, and after 1 week or longer, it is quantitative, i.e. no free acid anhydride can be detected by GC.

This reaction cannot be forced to completion by holding it for a longer time at 100° C., or by increasing the temperature, owing to the presence of a significant back-reaction. Furthermore, if the reaction temperature is increased, undesirable crosslinking is observed in the product, which is detected by size-exclusion chromatography (SEC). Eventually, the ester is eliminated to afford a partially dehydrated castor oil and carboxylic acid, which in the case of maleic acid can undergo the Diels-Alder reaction, as described above. Crosslinking is observed at about 125–150° C. and the Diels-Alder reaction at about 150–170° C. Accordingly, the reaction with maleic anhydride can be run at 120° C. for 4 hours with negligible crosslinking; however, the amount of free acid anhydride present at 120° C. is higher (about 1.5–2%) than at 100° C. (about 0.8–1.2%), and the time required for its disappearance at room temperature is correspondingly much longer.

Thus, a reaction temperature of about 75–120° C. is considered suitable, for a reaction time of about 4 to 24 hours; however, a temperature of about 100–120° C., depending on the carboxylic acid anhydride, is much preferred, for an initial reaction time of about 6–8 hours and a subsequent room temperature reaction time of about 1–2 weeks.

The invention will now be illustrated by the following examples, in which Examples 1–3 describe the process for making the high purity adducts of the invention, and Examples 4–5 describe skin care compositions containing such adducts.

EXAMPLE 1

A 2-I, four-neck round bottom flask is fitted with a heating mantle/temperature controller, agitator, nitrogen inlet tube, vacuum/atmospheric take off tube, and cold water condenser. The flask is charged with 1000.0 g (1.066 mol) of castor oil and 104.5 g (1.066 mol) (1:1 mole ratio) of maleic anhydride. The agitation is started and the air is evacuated from the system by applying full vacuum from a mechanical oil pump. After 5 minutes, the system is isolated from the vacuum pump and nitrogen is admitted to bring the pressure back to atmospheric. This evacuation-filling procedure is repeated two more times. A nitrogen sweep of 0.1 cubic foot per hour is set and the batch is quickly heated to 100° C. This temperature is held for 6–8 hours, until GC of two consecutive samples shows a conversion of 98.0% or higher. The batch is filtered at about 70–90° C. and allowed to cool to room temperature slowly over several hours. After 1–2 days, the conversion is 99.0% or higher and after 1–2 weeks, it is >99.9%, i.e. no free maleic anhydride is detectable by GC.

EXAMPLE 2

The apparatus described in Example 1 is charged with 150.0 g (0.16 mol) of castor oil and 16.0 g (0.16 mol) of succinic anhydride. The system is purged with nitrogen as described in the previous example and quickly heated to 120° C. After 4–6 hours, the conversion is 98–99% and the batch is filtered at 70–90° C. It is allowed to cool slowly to room temperature, where the conversion is 100% within 1–2 days.

EXAMPLE 3

The apparatus described in Example 1 is charged with 150.0 g (0.16 mol) of castor oil and 42.6 g (0.16 mol) of 2-dodecen-1-ylsuccinic anhydride (1:1 mole ratio). The system is purged with nitrogen as described in the first example and quickly heated to 120° C. After 8–12 hours, the conversion is 98–99% and the batch is filtered at 70–90° C. It is allowed to cool slowly to room temperature, where the conversion is >99.9% within 24 weeks.

EXAMPLE 4

TABLE 1

SKIN MOISTURIZER

| Phase | Ingredient | Formulation A | Formulation B |
|---|---|---|---|
| A | Deionized Water | 63.7 | 65.7 |
|   | Versene ® NA | 0.1 | 0.1 |
|   | Stabileze ® QM | 0.2 | 0.2 |
| B | Ceraphyl ® 230 | 4.0 | 4.0 |
|   | Ceraphyl ® 494 | 6.0 | 6.0 |
|   | Ceraphyl ® 368 | 10.0 | 10.0 |
|   | Cerasynt ® 840 | 2.0 | 2.0 |
|   | Cerasynt ® 945 | 6.0 | 6.0 |
| C | Deionized Water | 5.0 | 5.0 |
|   | 10% NaOH solution | 0.5 | 0.5 |
| D | Adduct of Ex. 1 | 2.0 | 0.0 |
| E | LiquaPar Optima | 0.5 | 0.5 |
|   | Total | 100.0 | 100.0 |

Preparation:
Combine water and Verse NA of phase A with stirring at room temperature. Slowly add Stabileze QM with stirring. Begin heating phase A to 70–75° C. with stirring. Combine ingredients of phase B, heat to 70–75° C. with stirring. When both phases have reached target temperature, add phase B to phase A with stirring. When addition is complete and mixture appears uniform, slowly add phase C. Once uniform, remove heat and maintain stirring. If present, add phase D at 50° C. Add phase E at 40° C. Continue stirring to room temperature.

Moisturization Measurement:
Identical amounts of Formulation A and Formulation B were applied to the right and left forearm of a volunteer and rubbed in. Measurements were made using a Skincon 200, which measures conductance, on both sites and adjacent untreated sites as a function of time. The greater the conductance, the greater the moisturization. The differences between treated and untreated sites were significant as was the difference between Formulation A and B showing that the adduct of the invention gives a substantial moisturization benefit from its formulation.

TABLE 2

| Time (min) | Control A ($\mu$-mho) | Formulation A ($\mu$-mho) | Control B ($\mu$-mho) | Formulation B ($\mu$-mho) |
|---|---|---|---|---|
| 10 | 8 | 45 | 12 | 31 |
| 20 | 10 | 31 | 6 | 24 |
| 30 | 10 | 27 | 13 | 23 |
| 40 | 8 | 37 | 6 | 22 |
| 50 | 15 | 28 | 11 | 26 |
| 60 | 7 | 27 | 11 | 24 |
| 70 | 17 | 28 | 17 | 23 |
| 80 | 15 | 21 | 15 | 25 |
| 90 | 16 | 36 | 15 | 30 |
| 110 | 8 | 29 | 11 | 24 |
| 130 | 6 | 19 | 6 | 20 |
| 160 | 7 | 17 | 5 | 11 |
| 180 | 9 | 18 | 7 | 13 |
| 220 | 9 | 19 | 7 | 13 |

EXAMPLE 5

TABLE 3

BODY WASH

| Phase | Ingredient | Amount (%) |
|---|---|---|
| A | Deionized Water | 5.7 |
|   | Versene ® NA | 0.1 |
|   | Gafquat ® 755N | 1.5 |
|   | Standopol ® ES-3 | 32.0 |
|   | Monamid ® CMA | 5.0 |
|   | Softigen ® 767 | 6.0 |
|   | Glycerin | 6.0 |
|   | Citric Acid | 0.1 |
|   | Stepan Mild LSB | 24.1 |
| B | Soybean Oil | 9.0 |
|   | Palmitic Acid | 4.5 |
|   | Adduct of Ex. 1 | 5.0 |
| C | Germaben ® II-E | 1.0 |
|   | TOTAL | 100.0 |

Preparation:
Combine deionized water, Versene® NA, Gafquat® 755N and Standopol® ES-3 at room temperature. Begin heating to 50° C. and add Monamid® CMA. Add remaining Phase A ingredients and heat to 70–75° C. Stir to uniformity after the addition of each ingredient. Combine ingredients of Phase B, heat to 70–75° C. and stir until uniform. Add Phase B to Phase A with stirring at 70° C. When batch appears uniform, turn off heat and continue stirring. Add Phase C at 40° C. Stir until room temperature.

Moisturization measurements were made using a Skincon® 200 after washing the forearm with both water and the body wash formulation.

TABLE 4

| Time (min) | Water ($\mu$-mho) | Body Wash ($\mu$-mho) |
| --- | --- | --- |
| 0 | 9 | 11 |
| 20 | 46 | 61 |
| 40 | 17 | 54 |
| 60 | 20 | 55 |
| 80 | 24 | 52 |
| 100 | 17 | 42 |
| 120 | 17 | 41 |
| 140 | 18 | 34 |
| 180 | 16 | 41 |
| 210 | 20 | 31 |
| 240 | 19 | 38 |
| 270 | 18 | 37 |
| 300 | 22 | 36 |
| 330 | 19 | 36 |
| 360 | 21 | 34 |

In summary, the high purity adducts of castor oil and cyclic carboxylic acid anhydrides, are characterized by the absence of free acid anhydride therein, and advantageous use in personal care products, such as skin care and hair care products. In such skin care compositions as body washes, a significant moisturization effect is achieved in both leave-on and rinse-off modes of application.

When the invention has been described with particular reference to certain embodiments thereof, it will be understood that changes and modifications may be made which are within the skill of the art. Accordingly, it is intended to be bound only by the following claims, in which:

What is claimed is:

1. A high purity adduct of castor oil and maleic anhydride characterized by the absence of free maleic anhydride.

2. An adduct according to claim 1 in which the mole ratio of maleic anhydride to castor oil is 0.5:1 to 1.5:1.

3. An adduct according to claim 1 in which said mole ratio is about 1:1.

4. A process for making the adduct of claim 1 with no side reactions comprising (a) reacting castor oil and maleic anhydride at a temperature of 75–120° C. for a reaction time of 4 to 24 hours, and then (b) continuing the reaction at room temperature for at least 1 week to make sure any remaining maleic anhydride has reacted.

5. A process according to claim 4 wherein (a) is carried out at about 100–120° C. for about 6–8 hours, and (b) is carried out at room temperature for about 1–2 weeks.

6. A personal care product including the adduct of claim 1.

7. A personal care product according to claim 6 which is a skin care composition.

8. A skin care product of claim 7 which is a body wash with significant moisturization in both leave-on and rinse-off modes of application.

9. A personal care product according to claim 6 which is a hair care composition.

10. The product of the process of claim 4.

* * * * *